United States Patent
Tornier et al.

(10) Patent No.: US 8,852,283 B2
(45) Date of Patent: Oct. 7, 2014

(54) GLENOIDAL COMPONENT, SET OF SUCH COMPONENTS AND SHOULDER PROSTHESIS INCORPORATING SUCH A GLENOIDAL COMPONENT

(71) Applicant: Tornier SAS, Saint-Ismier (FR)

(72) Inventors: Alain Tornier, Saint Ismier (FR); Francois Sirveaux, Villers les Nancy (FR); Gilles Walch, Lyons (FR); Daniel Mole, Nancy (FR); Christophe Levigne, Caluire (FR); Pascal Boileau, Nice (FR); Luc Favard, Montlouis (FR)

(73) Assignee: Tornier SAS, Montbonnot Saint Martin (FR)

( * ) Notice: Subject to any disclaimer, the term of this patent is extended or adjusted under 35 U.S.C. 154(b) by 0 days.

(21) Appl. No.: 13/664,197

(22) Filed: Oct. 30, 2012

(65) Prior Publication Data
US 2013/0060341 A1 Mar. 7, 2013

Related U.S. Application Data

(63) Continuation of application No. 11/147,177, filed on Jun. 8, 2005, now Pat. No. 8,303,665.

(60) Provisional application No. 60/579,284, filed on Jun. 15, 2004.

(30) Foreign Application Priority Data

Jun. 15, 2004 (FR) ...................................... 04 06471

(51) Int. Cl.
*A61F 2/40* (2006.01)
*A61F 2/30* (2006.01)
*A61B 17/86* (2006.01)
*A61F 2/46* (2006.01)

(52) U.S. Cl.
CPC ...... *A61F 2/30734* (2013.01); *A61F 2002/3023* (2013.01); *A61F 2220/0033* (2013.01); *A61F 2/4081* (2013.01); *A61F 2002/30433* (2013.01); *A61F 2/40* (2013.01); *A61F 2002/30332* (2013.01); *A61F 2002/30785* (2013.01); *A61F 2002/30797* (2013.01); *A61B 17/86* (2013.01); *A61F 2002/4638* (2013.01); *A61F 2/4059* (2013.01); *A61F 2002/4085* (2013.01); *A61F 2002/3038* (2013.01); *A61F 2002/4022* (2013.01); *A61F 2002/30736* (2013.01); *A61F 2002/30604* (2013.01); *A61F 2220/0041* (2013.01); *A61F 2230/0069* (2013.01); *A61F 2002/30878* (2013.01); *A61F 2002/3079* (2013.01); *A61F 2002/4062* (2013.01); *A61F 2002/30616* (2013.01); *A61F 2310/00011* (2013.01)
USPC ....................................................... 623/19.11

(58) Field of Classification Search
CPC A61F 2/40; A61F 2/30734; A61F 2002/3023
USPC ............................................ 623/19.11–19.14
See application file for complete search history.

(56) References Cited

U.S. PATENT DOCUMENTS 6,783,549 B1 * 8/2004 Stone et al. ................ 623/19.14

*Primary Examiner* — Bruce E Snow
(74) *Attorney, Agent, or Firm* — Knobbe Martens Olson & Bear, LLP

(57) ABSTRACT

This glenoidal component for a shoulder prosthesis comprises a base which may be immobilized on the glenoid cavity of a shoulder, and an element provided to be mounted on this base and forming a convex surface of articulation centered on an axis of symmetry. This axis of symmetry is non perpendicular to a rear face of the base intended to abut against the glenoid cavity, this making it possible to compensate a defect in parallelism between the resectioned surface of the glenoid cavity and the axis of the patient's spinal column.

A surgeon can select the component most adapted to the orientation of the resectioned surface from a set of components in which the axes of symmetry of the components are oriented differently with respect to their rear faces.

7 Claims, 5 Drawing Sheets

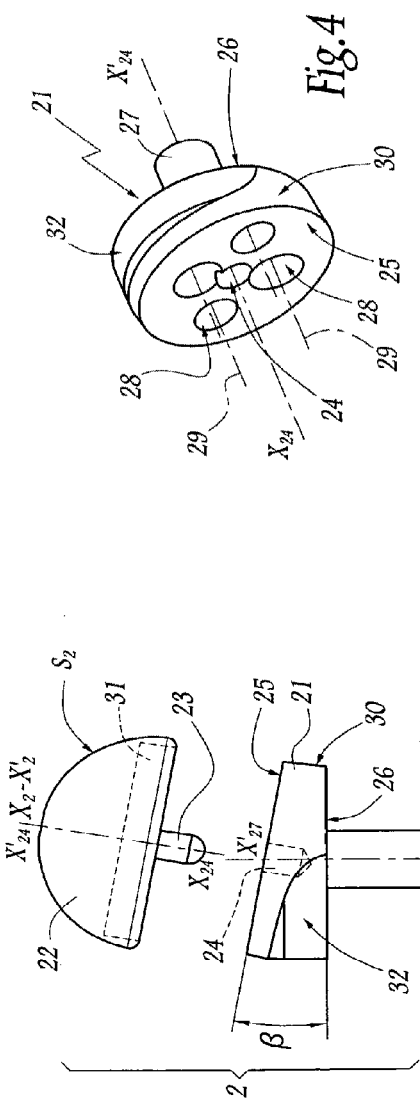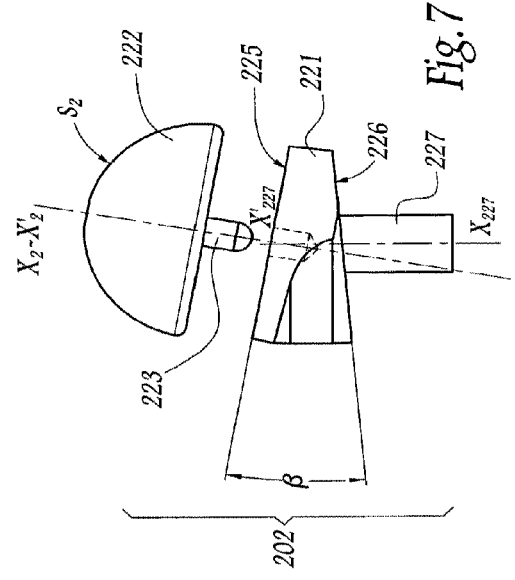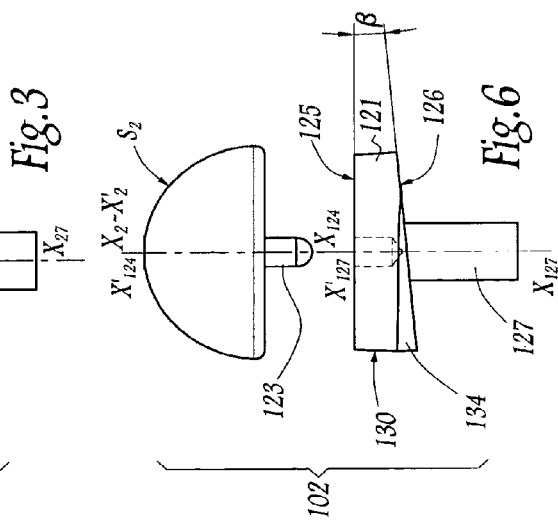

GLENOIDAL COMPONENT, SET OF SUCH COMPONENTS AND SHOULDER PROSTHESIS INCORPORATING SUCH A GLENOIDAL COMPONENT

FIELD OF THE INVENTION

The present invention relates to a glenoidal component of a shoulder prosthesis and to a set of such components that may be used for constituting a prosthesis. The invention also relates to a shoulder prosthesis comprising such a component as well as to a method for installing such a component.

BACKGROUND OF THE INVENTION

In the domain of shoulder protheses, it is known, for example from U.S. Pat. No. 3,978,528, to constitute a so-called "inverted" prosthesis in which a convex articular surface fast with the glenoid cavity and a concave articular surface fast with the humerus, cooperate in order to recreate a joint at the level of the shoulder. In this type of prosthesis, the glenoidal component may be formed, as disclosed in FR-A-2 835 425, by a base intended to be immobilized on the glenoid cavity and by an element intended to be mounted on this base and defining the convex surface of articulation.

Furthermore, it is known from FR-A-2 836 039, to provide a possibility of mounting an element forming a convex surface of articulation on a corresponding base in different positions, this allowing an adjustment of the articular surface in height with respect to the glenoid cavity.

The base of the known glenoidal components is provided with a so-called "rear face" intended to abut against a resectioned surface of the glenoid cavity which is normally substantially vertical when the patient is in standing position. Now, it may happen that the upper part of the scapula be worn out or destroyed, to the point of modifying the kinematics of the implant by the displacement of the original centre of rotation, this having for consequence to limit the movements of the patient's arm.

It is a particular object of the present invention to overcome these drawbacks by proposing a glenoidal component which ensures a correct positioning of the convex surface of articulation, including when the glenoid cavity is damaged or worn out in its upper part and even in its lower part.

SUMMARY OF THE INVENTION

In that spirit, the invention relates to a glenoidal component of a shoulder prosthesis which forms a convex surface of articulation centred on an axis of symmetry. This component is characterized in that the axis of symmetry of the convex surface of articulation is non perpendicular to a rear face of the component which is intended to abut against the glenoid cavity.

Thanks to the invention, the convex surface of articulation may be inclined downwardly or "slanted" with respect to the rear face of the component, this making it possible to orient this articular surface correctly, including when the bearing surface created in the glenoid cavity by resection is not parallel to the direction of the patient's spinal column. The invention therefore makes it possible to "compensate" a defect in parallelism between the resectioned surface of the glenoid cavity and the axis of the patient's spinal column.

According to advantageous but non-obligatory aspects, a glenoidal component may incorporate one or more of the following characteristics taken in any technically admissible combination:

In assembled configuration of the component and when the rear face is vertical, the axis of symmetry of the convex surface of articulation is directed downwardly, moving away from the rear face.

The component comprises a base adapted to be immobilized on the glenoid cavity of a shoulder and an element provided to be mounted on this base and defining the convex articular surface, while the base is provided with a substantially planar front face in which is pierced a housing for receiving a finger for centring the element forming the convex surface of articulation, this housing being centred on an axis substantially perpendicular to this front face, this front face not being parallel to the rear face of the base. In that case, the front and rear faces of the base may together form an angle included between 2° and 18°. The base may be provided with an axisymmetric surface centred on an axis perpendicular to its front face, this surface being adapted to cooperate with an internal surface of the afore-mentioned element for centring and immobilization thereof on the base.

The component may be provided with an anchoring stem which extends in a direction which is not perpendicular to at least a part of its rear face.

The component comprises a base adapted to be immobilized on the glenoid cavity of a shoulder and an element provided to be mounted on this base and defining the convex articular surface, while the element which forms the convex surface of articulation is provided with a skirt which is non-symmetrical with respect to the axis of the afore-mentioned surface, which extends this surface and in which is defined, at least in part, a housing for receiving at least a part of the base. This skirt may be substantially in the form of a portion of torus. The element which defines the convex surface of articulation is advantageously provided with a bore for passage of a member for manoeuvring a means for connecting this element on the base, this passage extending substantially in a direction globally perpendicular to this surface but not merged with its axis of symmetry.

The invention also relates to a set of glenoidal components for a shoulder prosthesis of the type defined hereinabove which allows a surgeon to select a component of appropriate geometry as a function of the effective configuration of the glenoid cavity once the latter is resectioned. This set of components is characterized in that the orientation of the axis of symmetry of the convex surface of articulation, with respect to a rear face of each component intended to abut against the glenoid cavity, is variable from one component to another.

According to a first variant embodiment, the front and rear faces of the bases of the components are not necessarily parallel to each other, in which case the angle between these front and rear faces is different from one component to another.

According to another variant, the elements of these components which form a convex articular surface may each be provided with a skirt, as mentioned hereinabove, the dimensions of the skirts being different from one component to another.

The invention also relates to a total shoulder prosthesis which comprises a glenoidal component as described hereinabove or selected from a set of components as described hereinabove.

Finally, the invention relates to a method for installing a glenoidal component of a total shoulder prosthesis, such a component defining a convex articular surface centred on an axis of symmetry, this method comprising steps consisting in:

milling the patient's glenoid cavity in order to create a bearing surface for the component, selecting, from a plurality of glenoidal components of which the axes of symmetry of the convex articular surfaces are oriented differently with respect to their bearing face against the resectioned surface of the glenoid cavity, a component which may be applied against this surface in such a position that the afore-mentioned axis of symmetry is globally perpendicular to the direction of the patient's spinal column, and immobilizing the selected glenoidal component on the glenoid cavity in the afore-mentioned position.

BRIEF DESCRIPTION OF THE DRAWINGS

The invention will be more readily understood and other advantages thereof will appear more clearly in the light of the following description of five forms of embodiment of a glenoidal component and of two forms of embodiment of a set of glenoidal components in accordance with its principle, given solely by way of example and made with reference to the accompanying drawings, in which:

FIG. 3 is an exploded side view of the glenoidal component used in the prosthesis of FIG. 2.

FIG. 4 is a view in perspective of a base belonging to the component shown in FIG. 3.

FIG. 6 is a view similar to FIG. 3 for a component in accordance with a second form of embodiment of the invention.

FIG. 7 is a view similar to FIG. 3 for a component in accordance with a third form of embodiment of the invention.

DESCRIPTION OF PREFERRED EMBODIMENTS

Figure 1:
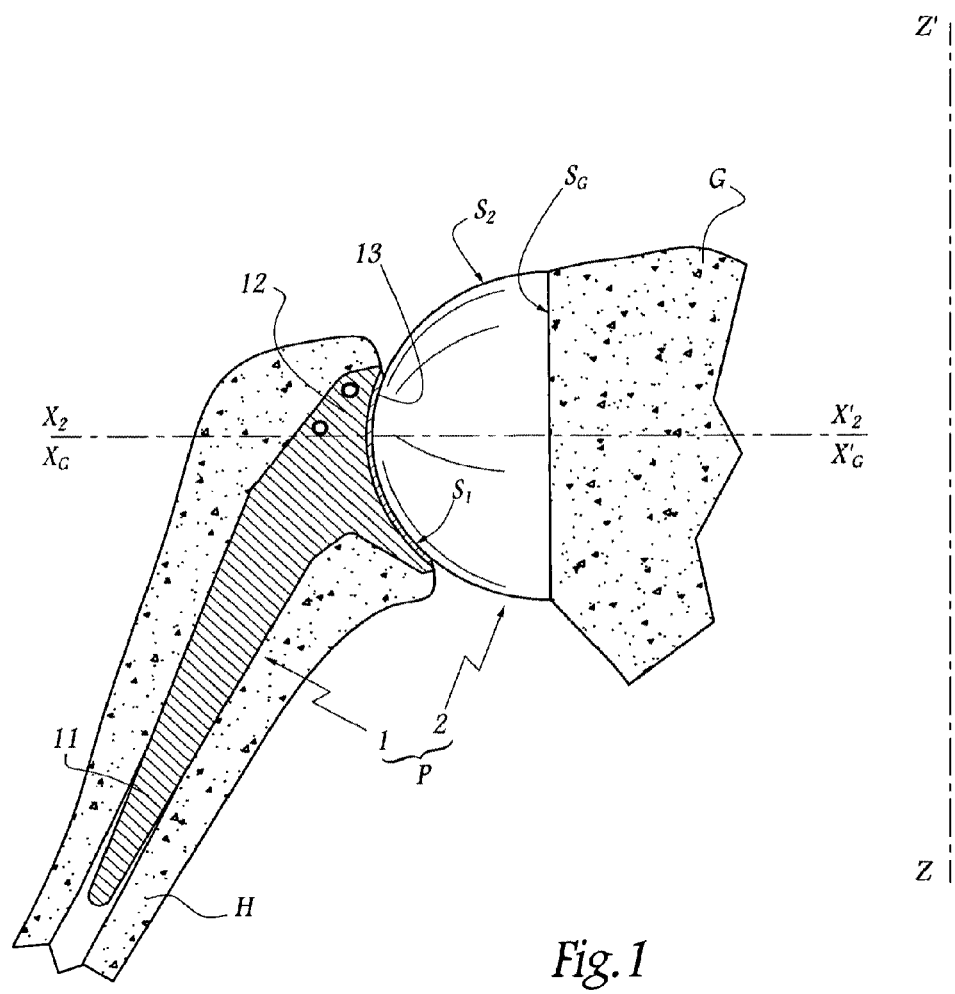
FIG. 1 schematically shows a shoulder prosthesis according to the invention implanted on a patient in a first configuration.

Referring now to the drawings, the prosthesis P shown in FIG. 1 comprises a humeral component 1 composed of a stem 11 intended to be anchored in the medullary canal of the humerus H, as well as of a metaphyseal part 12 in which is immobilized a cup 13 made of polyethylene defining a concave articular surface $S_1$ substantially in the form of a portion of sphere.

In accordance with a variant of the invention (not shown), the component 1 does not present a cup 13, the surface $S_1$ being formed by the metaphyseal part which is made of metal.

The prosthesis P also comprises a glenoidal component 2 which defines a convex articular surface $S_2$ substantially in the form of a hemisphere.

In order to render the drawing clearer, the component 1 is shown in section, while the component 2 is shown in an outside view in FIG. 1.

The surface $S_2$ is substantially in the form of a hemisphere and $X_2$-$X'_2$ denotes the axis of symmetry on which this surface is centred.

Furthermore, Z-Z' denotes a vertical axis passing through the centre of the spinal column of a patient who is standing up.

$S_G$ denotes the milled surface of the glenoid cavity G against which the component 2 abuts when it is mounted on the glenoid cavity.

Normally, the surface $S_G$ is substantially parallel to axis Z-Z', with the result that an axis $X_G$-$X'_G$ normal to the surface $S_G$ and passing through its centre, is substantially perpendicular to axis Z-Z', i.e. substantially horizontal when the patient is standing up. In the configuration of FIG. 1 which corresponds to a nominal configuration of implantation, axes $X_G$-$X'_G$ and $X_2$-$X'_2$ merge and are both horizontal.

Figure 2:
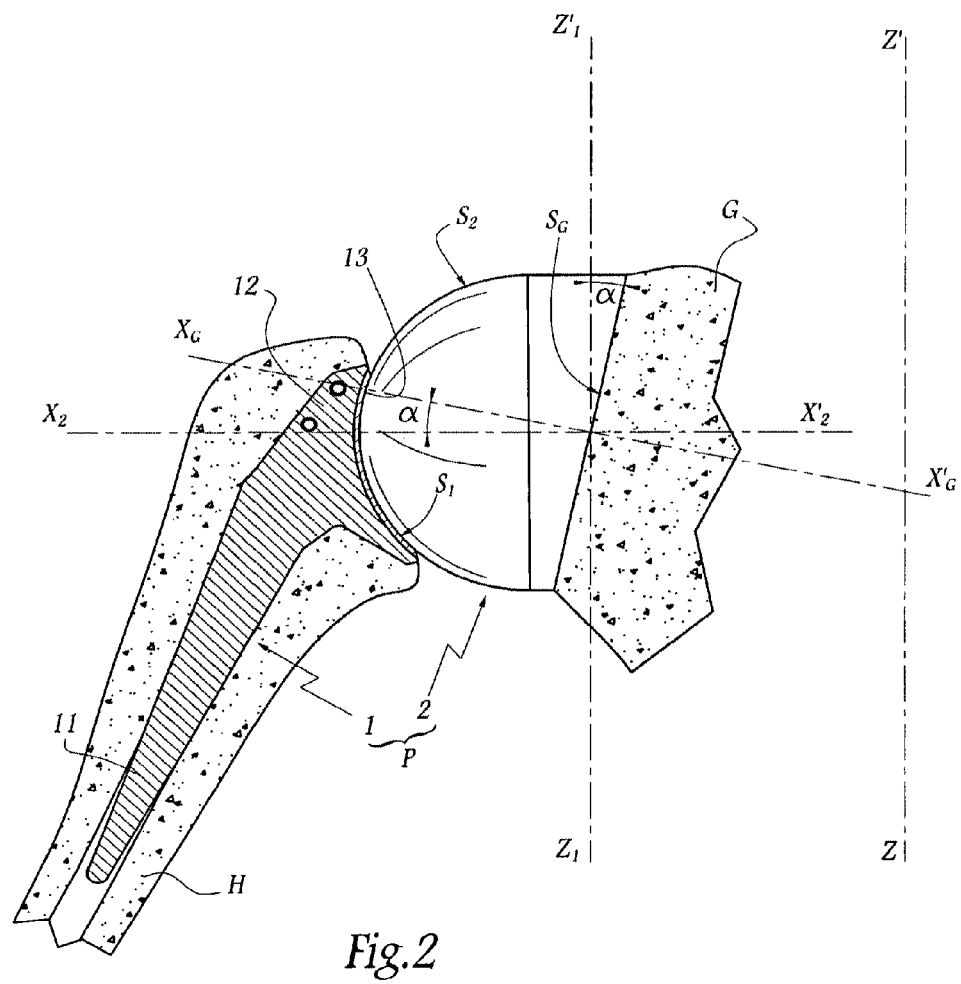
FIG. 2 is a view similar to FIG. 1 for a prosthesis likewise according to the invention, implanted in a second configuration.

However, as shown in FIG. 2, it may happen that the surface $S_G$ is not really parallel to the axis Z-Z', particularly due to wear of the glenoid cavity G or a partial destruction thereof in its upper part, and even its lower part. In that case, the surface $S_G$ forms a non-zero angle α with respect to a straight line $Z_1$-$Z'_1$ parallel to axis Z-Z' and passing through the centre $M_G$ of the surface $S_G$. When the patient is standing up, the axis $X_G$-$X'_G$ forms the same angle α with respect to the horizontal.

According to the invention, the component 2 is configured so that the axis $X_2$-$X'_2$ of the surface $S_2$ is substantially horizontal when the patient is standing up, despite the non-optimal orientation of the surface $S_G$.

The component 2 is shown in exploded side view in FIG. 3 and comprises a base or plate 21 intended to be fixed on the glenoid cavity G, as well as a metallic element 22, sometimes called "head", which defines the surface $S_2$ and which is provided with a centring finger 23 intended to penetrate in a housing 24 made in the base 21 and centred on an axis $X_{24}$-$X'_{24}$ perpendicular to the front face 25 of the base 21 which is substantially planar and oriented opposite the glenoid cavity when the base is mounted on the glenoid cavity.

26 denotes the rear face of the base 21 which bears against the surface $S_G$ when the base is in mounted configuration.

An anchoring stem 27 extends from the surface 26 in a direction parallel to an axis $X_{27}$-$X'_{27}$ perpendicular to the surface 26.

The base 21 is also pierced with four orifices 28 for passage of four screws 29 represented solely by their lines of axis in FIG. 4.

The front face 25 is in the form of a disc centred on the axis $X_{24}$-$X'_{24}$ and bordered by a truncated surface 30, centred on the axis $X_{24}$-$X'_{24}$ and convergent opposite the stem 27.

The surface 30 extends all around the front face 25 but joins the rear face 26 over only a part of the periphery of the base 21.

The face 26 is substantially planar and the faces 25 and 26 are not parallel to each other. β denotes the non-zero angle formed between the faces 25 and 26.

The inclined character of the front face 25 with respect to the rear face 26 of the base 21 makes it possible to "compensate" completely or partially the inclined character with respect to the straight line $Z_1$-$Z'_1$ of the surface $S_G$, as long as the least thick part of the base 21, which is shown to the right of FIG. 3, is disposed in the vicinity of the lower part of the surface $S_G$, i.e. the part located towards the patient's ribs.

When the base or plate 21 has been anchored on the glenoid cavity G as indicated hereinabove thanks to the stem 27 and to the positioning of the four screws 29, the element 22 may be placed in position by introducing the finger 23 in the housing 24 and causing an internal surface 31 of the element 22 shown in broken lines only in FIG. 3, to bear against the surface 30. The geometries of the surfaces 30 and 31 are adapted to obtain a locking in the manner of a Morse cone.

In this way, the relative orientation of the faces 25 and 26 makes it possible to orient the axis $X_2$-$X'_2$ of the surface $S_2$ downwardly in FIG. 2 with respect to axis $X_G$-$X'_G$ in its part which projects beyond the glenoid cavity, i.e. to return this axis into substantially horizontal configuration, while the surface $S_G$ is not parallel to axis Z-Z'.

Taking into account the relative orientation of the faces 25 and 26, the surface 30 borders the face 25 only over a fraction of the height of that part of the base located between the faces 25 and 26. 32 denotes the portion of peripheral surface of the base 21 which is not formed by part 30. This surface is out of true.

Figure 5:
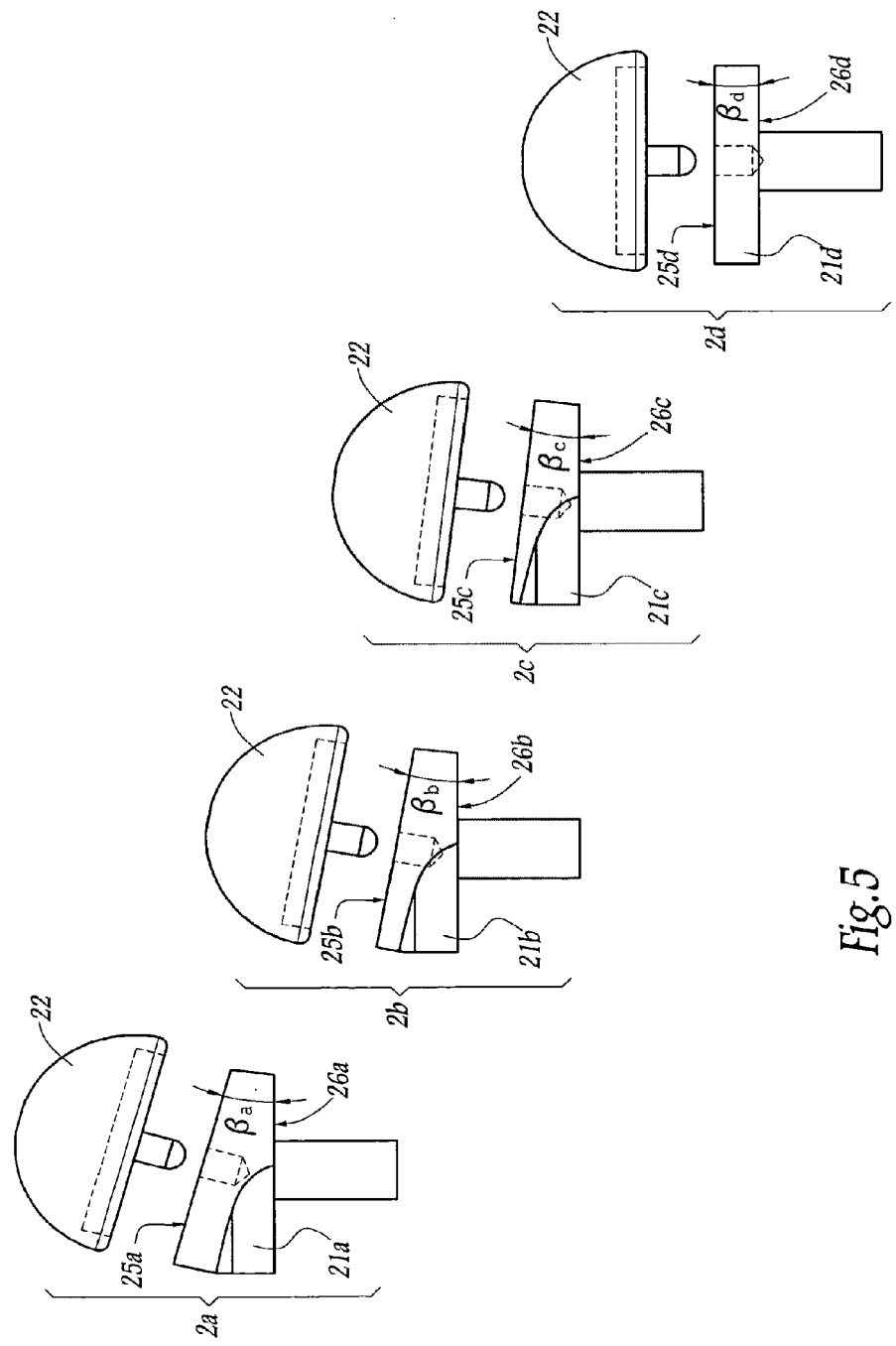
FIG. 5 schematically shows a set of glenoidal components incorporating the one shown in FIGS. 3 and 4.

As is more particularly visible in FIG. 5, a set of glenoidal components according to the invention may incorporate a plurality of glenoidal components 2a, 2b, 2c and 2d of which the bases 21a, 21b, 21c and 21d have front faces 25a, 25b, 25c and 25d which make different angles βa, βb, βc, βd with respect to their respective rear faces 26a, 26b, 26c and 26d. It will be noted that the front and rear faces of the base 21d are substantially parallel, the angle βd between them being, in that case, zero.

The element 22 associated with each base 21a, 21b, 21c and 21d may be the same or be different from one component to another.

In this way, when a surgeon installs a shoulder prosthesis P, he may, as a function of the relative orientation of the surface $S_G$ and of the axis Z-Z', select a glenoidal component of which the base comprises front and rear faces oriented in such a manner as to allow the main part of the defect of orientation of the surface $S_G$ to be compensated.

Of course, the number of glenoidal components of a set such as the one shown in FIG. 5 is not necessarily four. It may be chosen as a function of the desired precision. In addition, it is not compulsory that, in such a set, a plate has surfaces which are parallel to each other, as shown to the right in FIG. 5. However, it is noted that the glenoidal component shown to the right of FIG. 5 may be used when the prosthesis P is to be implanted in the configuration of FIG. 1.

The installation of a total shoulder prosthesis is facilitated by the use of such a set of components insofar as the surgeon can select a glenoidal component effectively adapted to the patient's morphology, then immobilize this component in a position such that the axis of symmetry of the convex articular surface is substantially perpendicular to the longitudinal axis of the patient's spinal column.

In the second form of embodiment of the invention shown in FIG. 6, elements similar to those of the first embodiment bear identical references increased by 100. The glenoidal component 102 of this embodiment comprises an element 122 which bears a substantially hemispherical convex articular surface, this element being identical to that of the first embodiment. The base 121 of the component 102 also comprises an anchoring stem 127. This anchoring stem is centred on an axis $X_{27}$-$X'_{27}$ perpendicular to the front face 125 of the base 121 which is planar and bordered by a truncated surface 130. The base 121 is provided with a housing 124 for receiving a finger 123 belonging to the element 122, this finger being centred on the axis of symmetry of the surface $S_2$. The central axis $X_{124}$-$X'_{124}$ of the housing 124 merges with the central axis $X_{127}$-$X'_{127}$ of the stem 127.

This form of embodiment differs from the preceding one in that the rear face 126 of the base 121 is not perpendicular to the axis $X_{127}$-$X'_{127}$, with the result that a non-zero angle β exists between the faces 125 and 126.

In this embodiment, it may be considered that the rear face 126 is provided with a "heel" or wedge 134 which serves to compensate the non-optimal orientation of the surface $S_G$.

In the third form of embodiment of the invention shown in FIG. 7, elements similar to those of the first embodiment bear identical references increased by 200. The glenoidal component 202 of this embodiment comprises a base 221 as well as an element 222 which forms a substantially hemispherical articular surface $S_2$ centred on an axis $X_2$-$X'_2$ on which a centring finger 223 is also centred.

The front (225) and rear (226) faces of the base 221 are not parallel to each other and define a non-zero angle β. This embodiment incorporates certain elements of the first and second embodiments, namely that the surfaces 225 and 226 are both inclined, in different directions, with respect to a longitudinal axis $X_{227}$-$X'_{227}$ of an anchoring stem 227 of the base 221 in the glenoid cavity.

Figure 9:
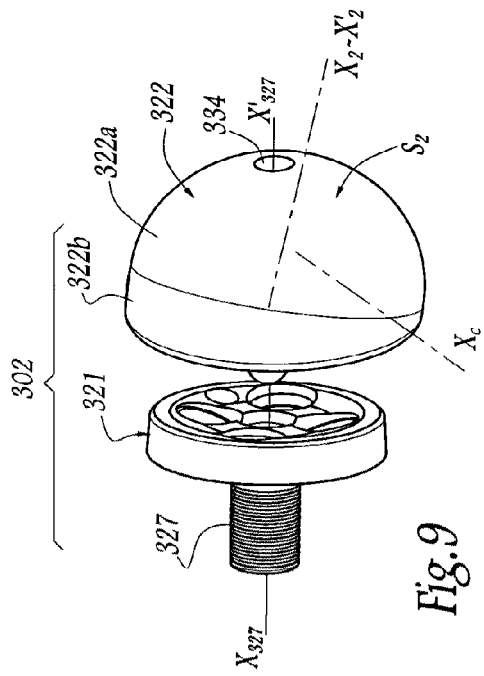
FIG. 9 is an exploded view in perspective of the component of FIG. 8.
Figure 11:
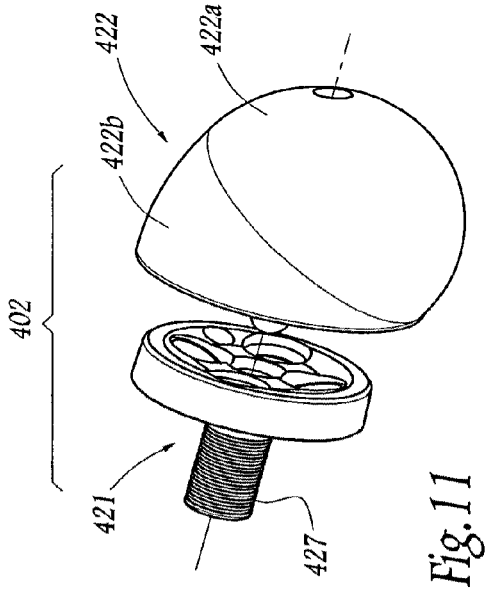
FIG. 11 is a view similar to FIG. 9 for the component of FIG. 10.
Figure 8:
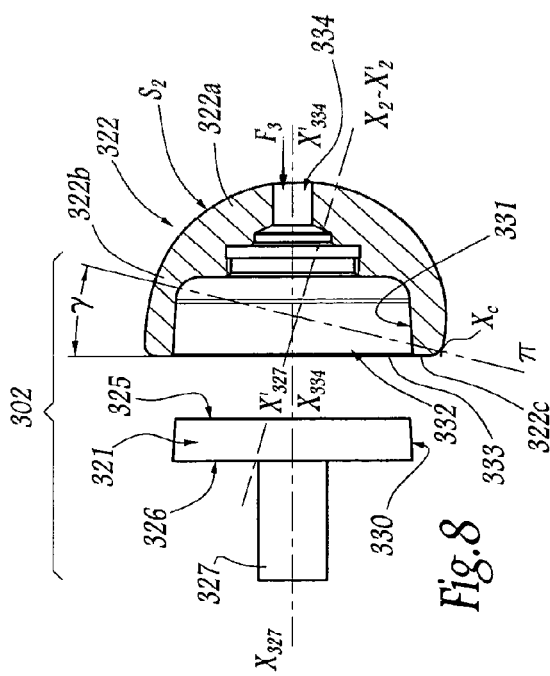
FIG. 8 shows a glenoidal component in accordance with a fourth form of embodiment of the invention of which the base is shown in side view and of which the element defining the convex articular surface is shown in cross section.

In the fourth form of embodiment of the invention shown in FIGS. 8 and 9, elements similar to those of the first embodiment bear identical references increased by 300. The glenoidal component 302 of this embodiment comprises a base 321 similar to that of the component shown to the right in FIG. 5, i.e. of to which the front (325) and rear (326) faces are substantially parallel to each other and perpendicular to a central axis $X_{327}$-$X'_{327}$ of an anchoring stem 327.

An element 322 intended to be mounted on the base 321 defines a surface $S_2$ substantially in the form of a hemisphere and centred on an axis $X_2$-$X'_2$ which is not parallel to axis $X_{327}$-$X'_{327}$ when the element 322 is in mounted configuration on the base 321. To that end, the portion 322a of the element 322 which defines the surface $S_2$ is extended by a skirt 322b in the form of a portion of torus centred on an axis $X_c$ perpendicular to axis $X_2$-$X'_2$ and tangential to the convex articular surface $S_2$ in the vicinity of a zone of intersection between this surface $S_2$ and a plane π perpendicular to axis $X_2$-$X'_2$ and passing through the centre $C_2$ of the surface $S_2$. γ denotes the angular amplitude of the skirt 322, i.e. the angle between the plane π and the rear face 322c of the element 322 intended to be turned towards the resectioned surface of the glenoid cavity when the component 302 is in mounted configuration.

A housing 332 is made inside the element 322, both in the skirt 322b and in the portion 322a. This housing is intended to receive the part of the base 321 defined between the surfaces 325 and 326. The housing 332 is bordered by a truncated surface 331 convergent in the direction of the surface $S_2$, while a surface 330 of the same geometry is provided on the element 321 between the faces 325 and 326.

333 denotes the circular opening for entrance in the housing 332.

The surface $S_2$ is pierced with a passage 334 allowing the introduction of a tool in the direction of arrow $F_3$ up to the interior of the element 322, which makes it possible to manoeuvre a screw (not shown) for immobilizing the element 322 on the base 321. Such a screw may in particular control the displacement of a finger such as the finger 23 of the first embodiment, which is, in that case, threaded, in order to be meshed with a tapped part of the base 321, and this in accordance with the technical teaching of FR-A-2 835 425.

$X_{334}$-$X'_{334}$ denotes the longitudinal axis of the passage 334. This axis is perpendicular to the surface $S_2$ and offset by angle γ with respect to axis $X_2$-$X'_2$.

Figure 10:
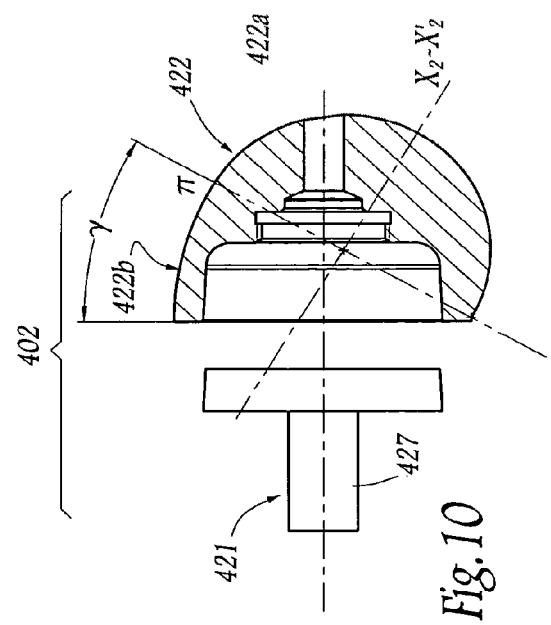
FIG. 10 is a view similar to FIG. 8 for a component in accordance with a fifth form of embodiment of the invention.

In the fifth form of embodiment of the invention shown in FIG. 10, elements similar to those of the first embodiment bear identical references increased by 400. The glenoidal component 402 of this embodiment is made in accordance with the same principle as that of the fourth embodiment, with a base 421 identical to base 321 and an element 422 which defines a surface $S_2$ centred on an axis $X_2$-$X'_2$ inclined downwardly in FIG. 10. This embodiment differs from the preceding one in that the angular amplitude γ of the skirt 422b, which extends the portion 422a of the element 422 defining the surface $S_2$, is greater than in the embodiment of FIGS. 8 and 9, this making it possible to increase the effect of cant of the surface $S_2$ with respect to the rear face 426 of the base 421.

The components shown in FIGS. 8 to 11 may be considered as belonging to the same set of glenoidal components allowing the surgeon to select the component most adapted as a function of the value of the angle γ and of the orientation of the resectioned surface $S_G$ of the glenoid cavity with respect to the longitudinal axis Z-Z' of the patient's spinal column.

Of course, the number of components of such a set is not limited to two.

The characteristics of the different forms of embodiment shown may be combined together in that a base or plate with non-parallel front and rear faces might be used with an element provided with a skirt extending the portion of this element defining an axisymmetric convex articular surface.

The invention also allows a correct implantation of a glenoidal component when the lower part of the scapula is damaged. In that case, it suffices to turn the component with respect to the configuration shown in FIG. 2.

The invention has been shown with two-part glenoidal components. However, it is equally well applicable to one-piece glenoidal components.

What is claimed is:

1. A plurality of glenoidal components for a shoulder prosthesis adapted to compensate defects in parallelism between a resected surface of a glenoid cavity and an axis of a patient's spinal column, the plurality of glenoidal components comprising:
    a first base comprising a front surface and a rear surface with an anchoring stem comprising a longitudinal axis, the longitudinal axis of the anchoring stem arranged at a first non-perpendicular angle with respect to the front surface and at a second non-perpendicular angle with respect to the rear surface, wherein the first non-perpendicular angle is different from the second non-perpendicular angle;
    a second base comprising a front surface and a rear surface with an anchoring stem comprising a longitudinal axis, the longitudinal axis of the anchoring stem arranged at a third non-perpendicular angle with respect to the front surface and at a fourth non-perpendicular angle with respect to the rear surface, wherein the third non-perpendicular angle is different from the fourth non-perpendicular angle; and
    a glenoid portion comprising a convex articular surface and a rear surface, the convex articular surface centered on an axis of symmetry, wherein the axis of symmetry is non-coincident with the longitudinal axis of the anchoring stem when the glenoid portion is engaged with one of the first base and the second base.

2. The plurality of glenoidal components of claim 1, wherein the front and rear surfaces of at least one of the first base and the second base form an angle with respect to each other between 2° and 18°.

3. The plurality of glenoidal components of claim 1, wherein the front and rear surfaces of the first base comprise a first surface angle that is different from a second surface angle formed by the front and rear surfaces of the second base.

4. The plurality of glenoidal components of claim 1, wherein the axis of symmetry is non-parallel to the longitudinal axis of the anchoring stem when the glenoid portion is engaged with the one of the first base and the second base.

5. The plurality of glenoidal components of claim 1, wherein the first base comprises a housing for receiving the glenoid portion, wherein the convex articular surface is centered on the front surface of the first base when the glenoid portion is engaged with the first base.

6. A plurality of glenoidal components for a shoulder prosthesis adapted to compensate defects in parallelism between a resected surface of a glenoid cavity and an axis of a patient's spinal column, the plurality of glenoidal components comprising:
    a first base comprising a front surface and a rear surface with an anchoring stem comprising a longitudinal axis, the longitudinal axis of the anchoring stem arranged at a first non-perpendicular angle with respect to the front surface and at a second non-perpendicular angle with respect to the rear surface, wherein the first non-perpendicular angle is different from the second non-perpendicular angle;
    a second base comprising a front surface and a rear surface with an anchoring stem comprising a longitudinal axis, the longitudinal axis of the anchoring stem arranged at a third non-perpendicular angle with respect to the front surface and at a fourth non-perpendicular angle with respect to the rear surface, wherein the third non-perpendicular angle is different from the fourth non-perpendicular angle;
    a first glenoid portion comprising a first convex articular surface and a first rear surface, the first convex articular surface centered on a first axis of symmetry, wherein the first axis of symmetry is non-coincident with the longitudinal axis of the anchoring stem of the first base when the first glenoid portion is engaged with the first base, and wherein the first axis of symmetry is non-coincident with the longitudinal axis of the anchoring stem of the second base when the first glenoid portion is engaged with the second base; and
    a second glenoid portion comprising a second convex articular surface and a second rear surface, the second convex articular surface centered on a second axis of symmetry, wherein the second axis of symmetry is non-coincident with the longitudinal axis of the anchoring stem of the first base when the second glenoid portion is engaged with the first base, and wherein the second axis of symmetry is non-coincident with the longitudinal axis of the anchoring stem of the second base when the second glenoid portion is engaged with the second base.

7. The plurality of glenoidal components of claim 6, wherein the first base comprises a housing for selectively receiving the first glenoid portion and the second glenoid portion, wherein the first convex articular surface is centered on the front surface of the first base when the first glenoid portion is engaged with the first base, and wherein the first convex articular surface is centered on the front surface of the second base when the first glenoid portion is engaged with the second base.

* * * * *